United States Patent [19]

Kornreich et al.

[11] Patent Number: 4,701,499
[45] Date of Patent: Oct. 20, 1987

[54] SYNTHESIS OF N-SUBSTITUTED PEPTIDE AMIDES

[75] Inventors: Wayne D. Kornreich; Harry A. Anderson, both of San Diego; John S. Porter, Leucadia; Jean E. F. Rivier, La Jolla, all of Calif.

[73] Assignee: The Salk Institute for Biological Studies, San Diego, Calif.

[21] Appl. No.: 799,339

[22] Filed: Feb. 3, 1986

Related U.S. Application Data

[62] Division of Ser. No. 545,077, Oct. 24, 1983.

[51] Int. Cl.[4] .................. C08F 8/18; C08F 12/08; C08F 112/08; C08F 212/08
[52] U.S. Cl. .................. 525/333.3; 525/333.4; 525/333.6; 525/54.11
[58] Field of Search ............... 525/333.3, 333.4, 333.6, 525/54.1, 54.11

[56] References Cited

U.S. PATENT DOCUMENTS 4,569,967  2/1986  Kornreich et al. ............ 525/54.11

Primary Examiner—John Kight
Assistant Examiner—Nathan M. Nutter
Attorney, Agent, or Firm—Fitch, Even, Tabin & Flannery

[57] ABSTRACT

Peptide N-alkylamides, and other C-terminal N-substituted amides, can be synthesized using solid-phase synthesis on a benzene-containing resin which is suitably methylated. Reactive amino groups are attached directly or indirectly to the methyl groups, for example, such as by reacting commercially available chloromethylated polystyrene resins with an alkylamine to create a resin-amine. The C-terminal amino acid of the desired peptide is linked to the resin-amine via an amide linkage, and the peptide is thereafter built in normal fashion. Treatment of the completed peptide intermediate with HF is effective to both effect deprotection and cleave the peptide from the resin in the form of the N-substituted amide. Examples include peptide N-ethylamides, N-fluoroethylamide, N-anilides and other substituted N-benzylamides.

8 Claims, No Drawings

SYNTHESIS OF N-SUBSTITUTED PEPTIDE AMIDES

This invention was made with Government support under NIH Contract No. 524,030, awarded by the National Institutes of Health. The Government has certain rights in this invention.

This is a division, of application Ser. No. 545,077, filed Oct. 24, 1983.

The invention relates to the synthesis of peptides and more particularly to the solid-phase synthesis of peptides using a styrene resin or the like in order to produce N-substituted peptide amides.

BACKGROUND OF THE INVENTION

The method presently available for solid-phase synthesis of C-terminal peptide N-substituted amides, such as N-ethylamide, using NαBoc and the usual side-chain-protecting groups, involves cleavage of a benzyl ester resin lingage by aminolysis using ethylamine. Following removal of excess ethylamine and separation from the resin, the protected peptide is deprotected using hydrogen fluoride(HF) and then purified via several steps. The method is inapplicable to peptides containing either Asp or Glu, protected as the benzyl ester, because these side chains will also undergo aminolysis. Thus, it has been heretofore necessary to synthesize such N-substituted peptides using classical synthesis or using some other suitable synthesis.

N-methyl amidated peptides have been successfully synthesized on an N-methyl benzhydrylamine resin, Rivier, J. et al., *J. Med. Chem.* 20, 1409 (1977); however, N-ethyl amidated peptides could not be successfully synthesized using the corresponding ethyl-substituted resin. Accordingly, improved methods for the solid-phase synthesis of N-substituted peptide amides were sought after.

SUMMARY OF THE INVENTION

It has now been found that such N-substituted peptide amides, such as peptide N-alkylamides, can be synthesized using solid-phase synthesis on a benzene-containing resin which has been suitably halomethylated, e.g. chloromethylated or bromomethylated, after the reactive amino groups are attached directly or indirectly to the methyl groups. For example, such a resin-amine can be provided by reacting commercially available chloromethylated polystyrene resins with an alkylamine. The C-terminal amino acid of the desired peptide is then linked to the resin-amine via an amide linkage, and the peptide is thereafter built in normal fashion. Treatment of the completed peptide intermediate with HF is effective to both effect deprotection and cleave the peptide from the resin in the form of the N-substituted amide.

DETAILED DESCRIPTION OF THE PREFERRED EMBODIMENTS

The fundamental premise of solid-phase peptide synthesis is that amino acids are assembled, generally one by one, into a peptide of a desired sequence while the amino acid residue which will be present at the carboxyl terminus is anchored to an insoluble support. Following the achievement of the desired sequence of amino acids on the support, a reagent is used to cleave the peptide chain from the support and liberate the completed peptide to solution. The individual amino acids may have side-chain protection in the completed form on the resin, and it is advantageous to be able to remove the side-chain protecting groups at the same time as the peptide is cleaved from the resin. As indicated above, this has previously been possible when peptides having an amidated C-terminus were synthesized using a benzhyldrylamine resin. The present invention provides a process for the solid-phase synthesis of peptides having N-substituted amides at the C-terminus by appropriately adapting a suitable resin prior to beginning the synthesis.

Any suitable resin can be employed which contains phenyl groups. Synthetic polymers of styrene are preferred as these have been used over the last decade for solid-phase synthesis. The polystyrene resin can be crosslinked for stability and insolubility using about 1 to 2% divinylbenzene, as is well known in the art. The phenyl groups of the polystyrene resin are then substituted to provide the desired substituted α-aminobenzyl groups which can be linked to a protected amino acid via an amide bond. Cleavage ultimately takes place between the benzyl group and the amino group, releasing the completed amidated peptide into solution.

The resins can be prepared in any suitable manner. Chloromethylated resins are commercially available and have been used extensively for solid-phase synthesis of peptides. In synthesizing peptide C-terminal N-alkylamides, it may be convenient to appropriately adapt a chloromethylated polystyrene resin by treating the resin with an appropriate alkylamine, such as ethylamine. Treatment of such a resin with ethylamine at about 4° C. for about twenty-four hours produces the N-alkyl-substituted aminobenzyl groups. Instead of the alkylamine, a fluoroalkylamine can be used to produce a resin designed to provide a desired N-fluoroalkyl-substituted amide. Resins for producing the N-methylamide, a N-fluoromethylamide, the N-ethylamide or a N-fluoroethylamide are readily provided in this manner.

In addition, higher amine-resins have been prepared using beads of polystyrene resin that have been copolymerized with 1-2% divinylbenzene and treated with an acyl chloride for about 6 hours at about 25° C. to produce the appropriate phenyl alkyl ketone. Thereafter, reductive amination is carried out using the Leukardt-Wallach reaction to create the N-alkyl-substituted benzyl amine. The N-ethyl, N-propyl and N-isopropyl-substituted amines are conveniently made in this fashion. The carboxyl group of the C-terminal amino acid is coupled to the secondary amine via an amide linkage, and the peptide is thereafter built using standard solid-phase synthesis. Cleavage with HF breaks the amino bond to the benzyl moiety producing the N-alkyl-substituted peptide amide. Resin-amines created in this fashion can be used to synthesize fluorinated lower alkyl amide peptides, such as N-2,2-difluoroisopropylamide peptides.

The method of the invention can also be used to synthesize peptide anilides and peptide substituted anilides. Such peptides are useful as chromogenic substrates to test the purity (i.e. activity) of enzymes, and they are generically referred to as enzyme substrates. Generally a para-nitroanilide peptide is used to assay for an action of a particular enzyme. The action of the enzyme splits off para-nitroaniline(pNA) from the C-terminus of the short peptide substrate, and by monitoring the rate of pNA formation, i.e., increase in absorbance per second, using a spectrophotometer, a determination can be made of the enzymatic activity which is present.

Resins suitable for the synthesis of such enzyme substrates in the form of peptide anilides are conveniently produced by starting with commercially available chloromethylated styrene resins. The resin can be treated with p-aminoaniline in dimethylformamide (DMF), using an appropriate amount of potassium fluoride as a catalyst, at about 80° C. for about 20 hours, creating N-aniline benzylamine moieties on the resin. Thereafter, the C-terminal amino acid is coupled to the primary amino group on the aniline via an amide bond with the carboxyl group, and the peptide chain is built as usual in solid-phase synthesis. The resultant peptidoresin is treated with HF at 0° C., breaking the amino bond to the benzyl moiety and producing the N-substituted p-aminoanilide peptide. Treatment with a peracid, e.g., perboric acid, perchloric acid or peracetic acid, with a transition metal oxide ion, e.g., potassium permanganate, or with a peroxide, e.g., $H_2O_2$ or $Na_2O_2$, oxidizes the p-aminoanilide to a p-nitroanilide.

Accordingly, the invention provides a method for synthesizing a peptide having a substituted amide at its C-terminus by solid-phase synthesis by preparing a synthetic resin having a plurality of benzyl moieties which are individually substituted with —NHQ, wherein Q is lower alkyl or lower fluoroalkyl or is benzene or substituted benzene, e.g., aniline or chlorobenzene. Thereafter, the synthetic resin is reacted with an amino acid having its alpha-amino group blocked (and having any labile side-chain group blocked) to cause a coupling of the carboxyl group thereof by an amide linkage to the substituent on the benzyl moiety. The amino acid choosen is of course the amino acid residue which is desired to be located at the C-terminus of the target peptide. After deblocking the alpha-amino group, additional protected amino acids are added in sequence to produce the desired peptide. Finally, the peptide is cleaved from the resin and simultaneously deprotected using hydrogen fluoride according to techniques commonly employed in solid phase peptide syntheses. For example, cleavage and the deprotection are commonly carried out using anhydrous HF at about 0° C. or slightly above. Alternatively, after treatment with HF, the peptidoresin mixture can be allowed to warm slowly to room temperature over a period of several hours.

The abbreviations for individual amino acid residues are conventional and are based upon the trivial name of the amino acid, e.g., pGlu is pyroglutamic acid, His is histidine, Trp is tryptophan, Ser is serine, Tyr is tyrosine, Gly is glycine, Leu is leucine, Arg is arginine, Pro is proline, Phe is phenylalanine, and Ala is alanine. Except for glycine, the amino acids referred to herein should be understood to be of the L-isomer configuration unless otherwise noted. Generally, solid phase synthesis is conducted in a manner so as to stepwise add the amino acids in the chain in the desired sequence as set forth in detail in U.S. Pat. No. 4,211,693, the disclosure of which is incorporated herein by reference. Side-chain protecting groups are preferably added to amino acids having labile side chains, such as Ser, Tyr, and Arg, as generallay known in the art and described in the text *Solid Phase Peptide Synthesis*, Stewart and Young (1969) W. H. Freeman and Co. The side-chain protecting group and a protecting group for the alpha-amino group are added to the individual amino acid before it is coupled to the chain being built upon the resin.

There are a number of well known classes of alpha-amino protecting groups, and any of these can be used. The preferred alpha-amino protecting group is tert-butyloxycarbonyl(Boc). The hydroxyl group of the serine is preferably protected by benzyl or 2,6-dichlorobenzyl(DCB). The phenolic group of Tyr is also suitably protected as by trityl or DCB. Likewise, the side-chain guanidino group of Arg or the amino group of Lys or the imidazole group of His are suitably protected with nitro, trityl or p-toluenesulfonyl(Tos). The criterion for selecting a side-chain protecting group is that it should be stable, under the reaction conditions, to the reagent selected for removing the alpha-amino protecting group at each step of the synthesis. The protecting group should not be split off under coupling conditions, but the protecting group should be removable upon completion of the synthesis of the desired amino acid sequence under reaction conditions that will not alter the peptide chain.

As previously indicated the fully protected peptide is cleaved from the resin, as generally well known in this art, and either simultaneously or subsequently deprotected. Preferably deprotection of the peptide, as well as cleavage of the peptide amide from the methylated styrene resin support, is accomplished using HF at a temperature of about 0° C. or slightly above, although the conclusion of the cleavage can be carried out at room temperature. Anisole is preferably added to the peptidoresin prior to treatment with HF. After removal of HF under vacuum, the cleaved, deprotected peptide is conveniently treated with ether, decanted, taken-up in dilute acetic acid, and lyophilized.

Thereafter, purification of the peptide is commonly effected by ion exchange chromotography on a CMC column, followed by partition chromotography, using a suitable elution system on a column packed with Sephadex G-25, or the like, or by using HPLC as well known in the art.

The following examples illustrate presently preferred methods for carrying out the invention and should be understood to be illustrative of, but not limiting upon, the scope of the invention, which is defined in the appended claims.

EXAMPLE I

[D-Trp$^6$, Pro$^9$-NHEt]-LRF having the following formula is prepared by solid phase synthesis: p-Glu-His-Trp-Ser-Tyr-D-Trp-Leu-Arg-Pro-NHCH$_2$CH$_3$.

A chloromethylated resin, which was prepared by the copolymerization of styrene with about 1% divinylbenzene, is used. About 10.0 grams of the resin are reacted with 100 ml of ethylamine at about 4° C. for about 24 hours with continuous stirring. As a result, the α-chlorobenzyl group is changed to the N-ethyl α-aminobenzyl group.

The C-terminal amino acid of the desired peptide, i.e., Pro, with its alpha-amino group suitably protected is then coupled to the resin by an amide bond to the secondary amino group on the resin. More specifically, coupling is carried out by standard DCC reagents mediating amide formation in about 1½ hours at room temperature.

Following the coupling of each amino acid residue, washing, deblocking and coupling of the next amino acid residue can be carried out in accordance with the following schedule using an automated machine or manually and beginning with about 5 grams of resin:

| Step | Reagents and Operations | Min Times Min |
|---|---|---|
| 1 | CH₂Cl₂ wash 80 ml (2 times) | 3 |
| 2 | Methanol (MeOH) wash 30 ml (2 times) | 3 |
| 3 | CH₂Cl₂ wash 80 ml (3 times) | 3 |
| 4 | 50 percent trifluoroacetic acid (TFA) plus 5 percent 1,2-ethanedithiol in CH₂Cl₂ 70 ml (2 times) | 10 |
| 5 | CH₂Cl₂ wash 80 ml (2 times) | 3 |
| 6 | Triethylamine (Et₃N) 12.5 percent in 70 ml of CH₂Cl₂ (2 times) | 5 |
| 7 | MeOH wash 40 ml (2 times) | 2 |
| 8 | CH₂Cl₂ wash 80 ml (3 times) | 3 |
| 9 | Boc-amino acid (10 mmoles) in 30 ml. of either DMF or CH₂Cl₂ depending upon the solubility of the particular protected amino acid, (1 time) plus dicyclohexylcarbodiimide (DCC) (10 mmoles) in CH₂Cl₂ | 30–300 |
| 10 | MeOH wash 40 ml (2 times) | 3 |
| 11 | MeOH wash 30 ml (2 times) | 3 |
| 12 | CH₂Cl₂ wash 80 ml (2 times) | 3 |

After step 12 if a manual process is being used, an aliquot is taken for a ninhydrin test: if the test is negative, go back to step 1 for coupling of the next amino acid; if the test is positive or slightly positive, go back and repeat steps 9 through 12.

The above schedule is used for coupling each of the amino acids of the peptide of the invention. N$^\alpha$Boc protection is used for each of the remaining amino acids throughout the synthesis until pGlu is reached. The side chain of Arg is protected with Tos. OBzl is used as a side chain protecting group for the hydroxyl group of Ser, and 2,6-dichlorobenzyl is used as the side chain protecting group for the hydroxyl group of Tyr. Tos is used as the side chain protecting group for His at the 2-position. pGlu is introduced as the benzyloxycarbonyl (Z) protected amino acid or as plain pGlu. The following amino acids, which have low solubility in CH$_2$Cl$_2$, are coupled using DMF or DMF:CH$_2$Cl$_2$ mixtures Boc-Leu H$_2$O, Boc-Arg(Tos), Boc-Trp and Z-pGlu or pGlu.

The peptide is deprotected and removed from the resin support by treatment with HF, adding 10 ml of anisole as a scavenger, stirring the resin in 50 ml. of HF at 0° C. and then allowing the stirred mixture to slowly warm to room temperature over a period of about 3 hours. HF is removed under vacuum, and the remainder is lyophilized to provide a crude peptide powder.

Purification of the peptide is effected by ion exchange chromatography on a CMC column, followed by partition chromatography using the elution system, n-butanol; acetic acid; water (4,1:5-volume ratio). The partition chromatography column is Sephadex G 25.

[D-Trp$^6$, Pro$^9$NHEt]-LRF is judged to be homogeneous using thin layer chromatography and several different solvent systems, as well as by using HPLC and an aqueous triethylammonium phosphate solution plus acetonitrile. Amino acid analysis of the resultant, purified peptide is consistent with the formula for the prepared structure, showing substantially integer-values for each amino acid in the chain. The optical rotation is measured on a photoelectric polarimeter $[\alpha]_D^{22} = -58.4°$ (c=1, 1% acetic acid).

Testing of the purified peptide shows that it has all of the physicochemical and biological properties of this nonapeptide substituted amide which had been earlier synthesized on a different resin, cleaved by aminolysis employing ethylamine and subsequently deprotected and purified.

EXAMPLE II

The process of Example I is repeated using 2,2,2-trifluoroethylamine in a solution of DMF and triethylamine (3 equivalents) at about 24° C. for about 48 hours, with continuous stirring, to create N-fluoroethyl α-aminobenzyl moieties on the cross-linked polystyrene resin.

The same reaction conditions set forth in Example I result in the synthesis of the nonapeptide substituted amide having the following formula:

pGlu-His-Trp-Ser-Tyr-D-Ala-Leu-Arg-Pro-NHCH$_2$CF$_3$.

EXAMPLE III

About 50 grams of resin beads of polystyrene that has been copolymerized with about 1% divinylbenzene are stirred at room temperature for about 2 hours in butyryl chloride with aluminum chloride as a catalyst, namely Friedel-Crafts conditions. Reaction occurs with the benzene moieties on the resin to form butyrophenone or propylphenylketone. These resulting ketone moieties are then subjected to the Leukardt-Wallach reduction amination reaction using N-propyl formamide to produce N-propyl α-aminobenzyl moieties. The step-by-step synthesis of the nonapeptide as set forth in Example I is repeated. Cleavage, deprotection and purification are carried out under the same conditions and are found to produce the nonapeptide amide having the following formula:

pGlu-His-Trp-Ser-Tyr-D-Trp-Leu-Arg-Pro-NHCH$_2$CH$_2$CH$_3$.

EXAMPLE IV

In order to produce an enzyme substrate material, a commercially available chloromethylated resin is initially obtained. About 50 grams of this resin is reacted with p-aminoaniline (50g) in 100 ml of DMF to which about 10 grams of KF have been added as a catalyst. The reaction is carried out, with stirring, at about 80° C. for about 20 hours. The synthetic resin is then washed with CH$_2$Cl$_2$ and CH$_3$OH and is ready for use in solid-phase synthesis. As a result of the reaction of the benzyl moieties are now substituted with NHC$_6$H$_4$NH$_2$.

The resin is then reacted with individual, protected amino acids in the manner set forth in Example I to create a desired tripeptide. The side chain of Arg is protected with Tos, and its alpha-amino group is protected with Boc. It is added to the resin by standard DCC coupling reaction in DMF for about 1.5 hours so that the carboxyl group of Arg couples via an amide bond to the primary amino group of the aniline substituent on the resin. Phe and D-Pro are then successively added to complete the synthesis of the tripeptide. Cleavage and removal of the Arg side chain-protecting and alpha-amino-protecting groups are carried out using HF at about 0° C. for about 2 hours. Purification is then carried out using the same general techniques as set forth with respect to Example I. Following completion of purification of the peptide, the amine group in the para-position on the aniline is oxidized to nitro using H$_2$O$_2$ at room temperature for about 2 hours. Thereafter, the pH of the solution is brought to about 2 using dilute HCl so as to produce the tripeptide hydrochloride salt having the formula: D-Pro-Phe-Arg-NH-φ-NO₂. HCl, which is lyophilized.

The testing of the tripeptide nitroanilide shows that it functions excellently as an enzyme substrate and is suitable for the detection of kallikreins, which liberates pNA having a distinctive chromatic yellow color detectable by UV/visible spectrophotometry.

EXAMPLE V

The resin produced in Example IV is used to form a tetrapeptide p-nitroanalide, namely: Bz-Ile-Glu-Gly-Arg-NH-φ-NO₂. HCl. When the last amino acid in the chain is added, i.e., Ile, its alpha-amino group is protected by benzoyl(Bz). The carboxyl side chain of Glu is protected with benzyl ester (Bzl). Cleavage and deprotection is carried out using HF at about 0° C. for 2 hours. The Bz protecting group at the N-terminus is not removed. Purification is carried out in the manner set forth in Example IV, and the amino group is oxidized to nitro using KMnO4 at about 25° C. for 48 hours. The pH is then adjusted to about 2 in order to provide the hydrochloride salt, having the formula: Bz-Ile-Glu-Gly-Arg-NH-φ-NO₂. HCl, which is extracted with CH₃OH, washed and lyophilized.

Testing shows that the enzyme substrate is functional and can be used, for example, to test for the presence of antitrypsin in plasma for the coagulating enzyme from the horseshoe crab, both of which liberate pNA.

Although the invention has been described with regard to certain perferred embodiments, it should be understood that various changes and modifications as would be obvious to one having the ordinary skill in the art may be made without departing from the scope of the invention which is set forth in appended claims. Particular features of the invention are emphasized in the claims which follow.

What is claimed is:

1. A resin for synthesizing a peptide having a substituted amide at the C-terminus thereof using solid-phase synthesis techniques, which resin comprises polystyrene that is suitably cross-linked to render it insoluble in DMF,
   a plurality of the phenyl groups of the polystyrene chains of the resin having been modified to form moieties of the formuloa —C₆H₄CH₂NHQ wherein Q is lower alkyl, lower fluoroalkyl, phenyl or substituted phenyl.

2. A resin in accordance with claim 1 wherein Q is ethyl.

3. A resin accordance with claim 1 wherein Q is fluoromethyl.

4. A resin in accordance with claim 1 wherein Q is fluoroethyl.

5. A resin in accordance with claim 1 wherein Q is propyl.

6. A resin in accordance with claim 1 wheren Q is C₆H₄NH₂.

7. A resin in accordance with claim 1 wherein Q is CH₂CF₃.

8. A resin in accordance with claim 1 wherein Q is CH(CH₃)₂.

* * * * *

UNITED STATES PATENT AND TRADEMARK OFFICE
CERTIFICATE OF CORRECTION

PATENT NO. : 4,701,499
DATED : October 20, 1987
INVENTOR(S) : Kornreich et al.

It is certified that error appears in the above-identified patent and that said Letters Patent is hereby corrected as shown below:

Column 5, line 3, Change "Min" to --Mix--,

Column 5, line 52, Change "(4,1:5-volume ratio)" to --(4:1:5-volume ratio)--.

Column 7, lines 2, 12 and 23, Change "$NO_2$. HCl" to $NO_2$ · HCl--.

Column 8, line 14, Correct the spelling of --formula--,

Column 8, line 19, After "resin", insert --in--,

Column 8, line 25, Correct the spelling of --wherein--.

Signed and Sealed this

Fifteenth Day of March, 1988

*Attest:*

DONALD J. QUIGG

*Attesting Officer*  Commissioner of Patents and Trademarks